United States Patent
Crivelii et al.

(10) Patent No.: US 8,572,459 B2
(45) Date of Patent: Oct. 29, 2013

(54) INSURING PROPER COMMUNICATION WITH CHOSEN IMPLANT AMONG MULTIPLE IMPLANTS IN PROXIMITY TO ONE ANOTHER

(75) Inventors: Rocco Crivelii, Bellinzona (CH); Alec Ginggen, Plymouth, MA (US)

(73) Assignee: Codman Neuro Sciences Sárl, LeLocle (CH)

( * ) Notice: Subject to any disclaimer, the term of this patent is extended or adjusted under 35 U.S.C. 154(b) by 1413 days.

(21) Appl. No.: 12/288,028

(22) Filed: Oct. 16, 2008

(65) Prior Publication Data

US 2010/0100203 A1    Apr. 22, 2010

(51) Int. Cl.
*H03M 13/00*    (2006.01)

(52) U.S. Cl.
USPC .......................................................... 714/758

(58) Field of Classification Search
USPC ................................................. 714/758, 700
See application file for complete search history.

(56) References Cited

U.S. PATENT DOCUMENTS

| | | | |
|---|---|---|---|
| 4,049,004 | A | 9/1977 | Walters |
| 5,800,473 | A | 9/1998 | Faisandier |
| 5,917,840 | A | 6/1999 | Cheney |
| 6,073,049 | A | 6/2000 | Alt et al. |
| 6,512,954 | B2 | 1/2003 | Fox et al. |
| 6,687,546 | B2 | 2/2004 | Lebel et al. |
| 6,758,810 | B2 | 7/2004 | Lebel et al. |
| 6,768,425 | B2 | 7/2004 | Flaherty et al. |
| 6,792,311 | B2 | 9/2004 | Fox et al. |
| 6,811,533 | B2 | 11/2004 | Lebel et al. |
| 7,069,552 | B2 | 6/2006 | Lindberg et al. |
| 7,110,823 | B2 | 9/2006 | Whitehurst et al. |
| 7,737,862 | B2 * | 6/2010 | Watanabe ................. 340/12.51 |

(Continued)

FOREIGN PATENT DOCUMENTS

| | | | |
|---|---|---|---|
| EP | 1498082 A1 * | 1/2005 | |
| WO | 99/49695 | 9/1999 | |
| WO | 2005/091540 | 9/2005 | |
| WO | WO 2007057049 A1 * | 5/2007 | |

OTHER PUBLICATIONS

Interdigital: "Updated Recommendation for UE-specific CRC", Internet Citation, Nov. 5-7, 2001, XP002345604, Retrieved from the Internet: URL:http://www.3gpp.org/ftp/tsg_ran/WG1_RL1 (retrieved on Sep. 19, 2005) (3 pages).

(Continued)

*Primary Examiner* — Albert Decady
*Assistant Examiner* — Enam Ahmed
(74) *Attorney, Agent, or Firm* — Cheryl F. Cohen

(57) ABSTRACT

A system and method for restricting proper regulation by a control unit of only the functionality of the targeted device whose operations are intended to be programmed so as to insure no adverse regulation of functionality with respect to any other non-targeted device. A memory associated with each of the control device and the targeted device stores a unique identification assigned to that targeted device compressed using an error detection scheme, wherein the compressed unique identification has a length less than or equal to that of each of the messages. Circuitry, such as a logic function, mixes the stored compressed unique identification with each message transmitted between the two devices subsequent to receipt of a response signal from the targeted device to an interrogation command from the control device to insure proper communication between the control device and the targeted device.

26 Claims, 2 Drawing Sheets

(56) References Cited

U.S. PATENT DOCUMENTS

| | | |
|---|---|---|
| 7,836,378 B2 * | 11/2010 | Shaeffer et al. ............... 714/763 |
| 2004/0024429 A1 | 2/2004 | Daly |
| 2004/0260363 A1 | 12/2004 | Arx et al. |
| 2009/0055709 A1 * | 2/2009 | Anderson et al. ............. 714/758 |
| 2010/0179707 A1 * | 7/2010 | Cannon et al. ................ 700/295 |

OTHER PUBLICATIONS

European Search Report in counterpart EP Application No. 09252415.6, dated Nov. 27, 2012 (10 pages).

* cited by examiner

US 8,572,459 B2

INSURING PROPER COMMUNICATION WITH CHOSEN IMPLANT AMONG MULTIPLE IMPLANTS IN PROXIMITY TO ONE ANOTHER

BACKGROUND OF THE INVENTION

1. Field of the Invention

The present invention is directed to a system and method for ensuring proper communication between two electronic devices in wireless communication.

2. Description of Related Art

Electronic devices are capable of communicating with one another either via a wire or wireless link. For instance, a control device or programmer may be employed to control the operation of another electronic device. If multiple electronic devices subject to being programmed by the control device are within communication range of one another then the control signals may undesirably and unintentionally regulate the operations of a non-targeted or unintended electronic device rather than a targeted electronic device whose operations are intended to be controlled.

By way of illustrative example, an external control device disposed outside the body may be used to control operations of an implantable medical device. When two or more medical devices are implanted in a patient and each is within the specified vicinity for proper communication with the control device, the programming signal transmitted from the control device may be undesirably received by a non-targeted implantable medical device thereby potentially causing an unwanted change in its operation. This is particularly problematic when the non-targeted device is used to control a life sustaining activity, such as a pacemaker or defibrillator.

It is therefore desirable to develop an improved apparatus and system for restricting proper regulation by the control unit of only the functionality of the targeted device whose operations are intended to be programmed and no adverse regulation of functionality with respect to any other non-targeted device.

SUMMARY OF THE INVENTION

The present invention is directed to a system and method for restricting proper regulation by a control unit of only the functionality of the targeted device whose operations are intended to be programmed so as to insure no adverse regulation of functionality with respect to any other non-targeted device.

An aspect of the present invention is directed to a system including a control device having control device processing circuitry and control device communication circuitry. A targeted device is in communication with the control device via messages transmitted by a wireless communication interface, wherein the targeted device includes targeted device processing circuitry and targeted device communication circuitry. Each of the control device and the targeted device has an associated memory device for storage of a compressed unique identification assigned to that targeted device, wherein the compressed unique identification has a length less than or equal to that of each of the messages. In a preferred embodiment, the unique identification is compressed using an error detection scheme, for example, a Cyclic Redundancy Check scheme. The control device processing circuitry and targeted device processing circuitry each includes circuitry for mixing of the stored compressed unique identification with each message transmitted between the two devices subsequent to receipt of a response signal from the targeted device to an interrogation command from the control device to insure proper communication between the control device and the targeted device. The mixing circuitry preferably comprises circuitry for performing a logic function (e.g., XOR) with the compressed unique identification. The unique identification can be assigned to the targeted device at the time of manufacture and the compressed unique identification is stored in the memory associated with the targeted device at the time of manufacture. In addition, the processing circuitry associated with each of the control device and the targeted device may further comprise circuitry for encoding the mixed result, wherein the mixed result is preferably encoded using a Manchester encoding scheme.

Another aspect of the present invention is directed to a method for insuring communication of messages between a control device and a targeted device programmable by the control device via a wireless communication interface. Initially, a unique identification associated with the targeted device is compressed to a length less than or equal to a length of each of the messages. The unique identification is preferably compressed using an error detection scheme, for example, a Cyclic Redundancy Check scheme. Communication is then initiated between the two devices by transmitting an interrogation command from the control device to the targeted device. In response to receiving the interrogation command at the targeted device, transmitting a response signal thereto that includes the compressed unique identification associated with the targeted device. The compressed unique identification is then extracted from the response signal received by the control device. Thereafter, the compressed unique identification is mixed with each subsequent message transmitted between the two devices to insure proper communication between the control device and the targeted device. In a preferred embodiment, the mixing entails, for each of the subsequent messages, performing a logic function (e.g., XOR) with the compressed unique identification. The unique identification is assigned to the targeted device at the time of manufacture and the compressed unique identification is stored in a memory associated with the targeted device at the time of manufacture. Preferably, the mixed result is encoded, for example, using a Manchester encoding scheme.

Yet another aspect of the present invention is directed to a system including a control device having control device processing circuitry and control device communication circuitry. A targeted device is in communication with the control device via messages transmitted by a wireless communication interface, wherein the targeted device includes targeted device processing circuitry and targeted device communication circuitry. Each of the control device and the targeted device has an associated memory for storage of a unique identification assigned to that targeted device. The control device processing circuitry and the targeted device processing circuitry each includes additional circuitry to insure proper communication between the control device and the targeted device. For each message transmitted between the two devices subsequent to a response signal transmitted from the targeted device to the control device following an initial interrogation signal from the control device to initiate communication between the two devices, the additional circuitry performing the following functions: (i) when the unique identification of the targeted device has a length that is longer than a length of the message, increasing the length of the message so as to be at least equal to the length of the unique identification; and (ii) mixing the lengthened unique identification with the message. In a preferred embodiment, the mixing circuitry comprises circuitry for performing a logic function (e.g., XOR) with the compressed unique identification. The unique identification is assigned to the targeted device at the time of manufacture and the compressed unique identification is stored in the memory associated with the targeted device at the time of manufacture.

Still another aspect of the present invention relates to a method for insuring communication of messages between a control device and a targeted device programmable by the control device via a wireless communication interface. Communication is initiated between the two devices by transmitting an interrogation command from the control device to the targeted device. In response to receiving the interrogation command at the targeted device, a response signal is transmitted thereto that includes a unique identification associated with the targeted device. The unique identification is extracted from the response signal received by the control device. For each subsequent message transmitted between the two devices to insure proper communication between the control device and the targeted device: (i) when the unique identification has a length that is longer than a length of the message, increasing the length of the message so as to be at least equal to the length of the unique identification; and (ii) mixing the lengthened unique identification with the message. In a preferred embodiment, the mixing comprises, for each of the subsequent messages, performing a logic function (e.g., XOR) with the compressed unique identification. The unique identification is assigned to the targeted device at the time of manufacture and the compressed unique identification is stored in a memory associated with the targeted device at the time of manufacture.

BRIEF DESCRIPTION OF THE DRAWINGS

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

The present invention will be shown and described by way of illustrative example for an implantable medical device controlled wirelessly via an external control device. It is, however, contemplated and within the intended scope of the present invention to employ the present invention for any communication between a control device (irrespective of whether it is external) and an associated targeted electronic device in which the control device is in wireless communication, wherein neither the control device nor the electronic device need be limited to the medical field.

Two or more medical devices may be located within the communication range of a control device used to program these devices. In such situation, there is a possibility when sending a communication from the control device to the targeted or intended medical device to undesirably and unintentionally regulate or program a non-targeted medical device in its vicinity. In one scenario, a single patient may have implanted therein multiple medical devices. Another possible situation is when multiple patients each having at least one implanted medical device are all within communication range of the same control device. Any case in which there are multiple programmable devices in the vicinity of the control device, the present invention restricts the control device to communicate with only the targeted programmable device avoiding unwanted regulation of the other non-targeted programmable device(s).

Figure 1:
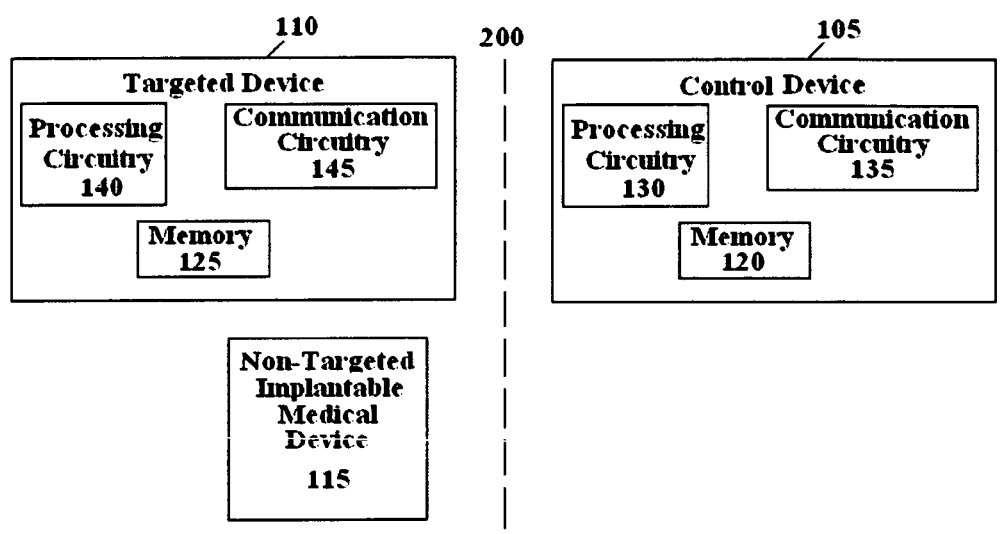
FIG. 1 is an exemplary schematic diagram of an implantable medical device wirelessly programmed via an external control device using the system and method in accordance with the present invention.

FIG. 1 depicts an exemplary medical communication system 100 between a control device 105 and a targeted implantable device 110 separated by a boundary 200 (e.g., skin). Also shown in FIG. 1 is another non-targeted implantable device 115. A single non-targeted implantable device is shown, however, more than one is possible. The non-targeted implantable device 115 may be regulated or controlled by its own control device (not shown), separate from that of control device 105. Otherwise, a single control device 105 may be used to program both implantable devices 110, 115. Each of the control unit 105 and targeted implantable medical device 110 also includes processing circuitry 130, 140, respectively, and communication circuitry 135, 145, respectively.

To initially establish communication the control device 105 generates an interrogation or identification command signal that is transmitted to the targeted implantable medical device 110. In turn, the implantable medical device 110 transmits back to the control device 105 an acknowledgement or response signal that includes an identification unique to the implantable medical device that is preferably assigned at the time of manufacture. The unique identification may be letters, numbers, symbols and/or any combination thereof, or any other unique identification for distinguishing one device from another.

This unique identification information can be inserted into the acknowledgement or response signal generated by the implantable medical device at a specified location such as at the beginning, the end or some other predetermined location in the signal. Upon receiving the response signal, the control device 105 extracts the unique identification information associated with the implantable medical device 110 based on its predetermined location and stores it in an associated memory 120 (e.g., Flash memory). The memory 120 may be either part of the control device 105 or external thereto.

Once communication has been established between the control device and the targeted implantable medical device, the link is maintained until communication ceases irrespective of movement of the implantable medical device. During subsequent communications, the targeted implantable medical device 110 is recognized based on its unique identification information. Communication is restricted to only that targeted implantable medical device 110 having its corresponding unique identification information stored in the memory 120 associated with the control device 105 at the beginning or start of communication when extracted from the response signal sent by the targeted implantable medical device 110. The unique identification information is included in all subsequent data packets, telegrams or messages transmitted between the targeted implantable medical device 110 and the control device 105. Specifically, the unique identification information is included in all data packets, telegrams or messages: (i) from the targeted implantable medical device 110 to the control device 105; and (ii) from the control device 105 to the targeted implantable medical device 110. It is desirable to include the identification information in all communications between the control device and targeted implantable medical device to recognize an improper communication transmission as quickly as possible. If the identification information is only provided in one telegram or message without any verification in subsequent communications between the devices then a non-targeted implantable medical device may be unintentionally regulated without discovering this error. By verifying the identification information with each transmission, any possible error in communication will be promptly detected.

As discussed above, the signal generated by the target implantable medical device 110 in response to the interrogation signal from the control device 105 will include the unique identification inserted at a predetermined location in the data packet, telegram or message thereby undesirably increasing its overall length. Inserting such unique identification at a predetermined location in the message permits the control device 105 to extract the unique identification from the response signal to be stored it in its memory 120 for future use. Once this initial operation has been performed and the unique identification for the targeted implantable medical device 110 has been communicated, for all subsequent communications between the control device 105 and implantable medical device, the unique identification information is inserted in a predetermined location of the message, for example, the beginning of the message, the end of the message, or any location therebetween. Such approach, however, would undesirably increase the overall size or length of the telegram and therefore the transmission time.

In order to avoid any increase in transmission time, the identification information transmitted with all communications subsequent to the acknowledgement or response signal from the targeted implantable medical device 110 to the initial read or interrogation signal from the control device 105 is preferably included in the message without increasing its size. One way to accomplish this result is to mix the identification information associated with the targeted implantable medical device with the message based on a logic function, such as an Exclusive-OR (XOR). Other logic functions may be utilized, as desired.

The mixing operation is limited, however, in that it requires that the length (e.g., the number of bytes) representative of the identification information be equal to or shorter than the length (e.g., the number of bytes) of the message. Under certain circumstances, the identification information may be greater in length than that of the message with which it is to be mixed precluding application of the logic function. To insure that that the length of the unique identification information is equal to or shorter than that of the message, the unique identification information is preferably compressed to a predetermined length, most preferably two bytes, before mixing with the message. Compression of the identification information to a predetermined length may be realized using a compression scheme. In the preferred embodiment, a Cyclic Redundancy Check (CRC) scheme is used to compress the identification information but other error detection schemes are contemplated and within the intended scope of the present invention. CRC schemes are conventionally used to detect the occurrence of data corruption. Whereas, in the present invention the CRC scheme is used for data compression. Error detection schemes are preferred because conventional data compression schemes would not sufficiently compress the data string to the desired length, e.g., from a 9-byte data stream reduced to 2-bytes, without the undesirable loss of information. Furthermore, compression schemes are not analogous to error detection schemes because the original information signal may be recovered from an encoded signal if the specific compression scheme utilized is known; however, this is not the case when applying an error detection scheme. That is, the original information signal is not recoverable from the CRC result based on the CRC algorithm.

Figure 2:
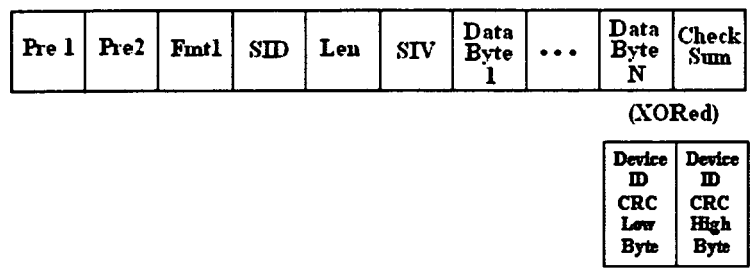
FIG. 2 is an exemplary telegram communication between the control device and the targeted implantable medical device of FIG. 1 wherein each message communicated between the two devices subsequent to the acknowledgement response signal from the targeted implantable medical device is mixed with a CRC compressed 2-byte unique identification information assigned to the targeted implantable medical device.

By way of illustrative example, the unique identification information of the targeted implantable medical device 110 is 9-bytes in length. This unique identification is reduced in accordance with the present invention from 9-bytes to 2-bytes using CRC and the 2-byte compressed unique identification (Device ID CRC low and Device ID CRC high) is stored in a memory 125 (e.g., a Flash memory) associated with the targeted implantable medical device 110, preferably stored during manufacture. Memory 125 is depicted as part of the targeted implantable medical device 110; alternatively, memory 125 may be external thereto. When the targeted implantable medical device 110 receives an initial communication signal (e.g., interrogation or read device identification signal or command) invoked by the control device 105, the targeted implantable medical device 110 transmits back a response signal that includes the 2-byte compressed unique identification as retrieved from the Flash memory 125. Since the unique identification of the targeted implantable medical device 110 is passed to the control device 105 at a first instance as part of the interrogation or read device identification command, the compressed unique identification of the targeted implantable medical device (Device ID CRC low and Device ID CRC high) is not XORed with the command and its acknowledgement, or response and its acknowledgement telegrams. For all subsequent communications between the targeted implantable medical device 110 and the control device 105, the 2-byte compressed unique identification (Device ID CRC low and Device ID CRC high) is XORed with two bytes of the message. In the example shown in FIG. 2, the 2-byte compressed unique identification (Device ID CRC low and Device ID CRC high) is XORed with the last two bytes of the message (the last data byte (Data byte N) and the check sum byte (CS8)) but any other predetermined 2-bytes of the message may be selected such as the first 2-bytes or any 2-bytes in the message. Lastly, Manchester encoding is performed on the XORed logic result prior to transmission.

Thus, far the present invention has described compression of the unique identification to insure that it does not exceed the length of the message with which it is to be mixed. Alternatively, the length of the message may be increased by adding additional bytes to insure that its length is greater than or equal to that of the unique identification. This alternative scheme would undesirably increase the overall communication time due to the increased length of the telegram being transmitted.

The example described herein is for illustration purposes only and not intended in any way to limit the scope of the present invention. In particular, the initial length of the unique identification need not be limited to 9 bytes, but instead may be any desired length. Compression of the unique identification is preferably reduced to only two bytes, but once again the number of compressed unique identification may be selected, as desired. The logic function performed is not limited to the XOR function nor is the specific error detection scheme restricted to that described in the example above.

Accordingly, the present invention substantially reduces or prevents the control device from programming an unintended or non-targeted device when more than one possible device is located within the wireless communication range of the control device. If the implantable medical device receives a message from a control device with a unique identification different from its own, the implantable medical device will discard the message and not send any acknowledgement or response message back to the control device.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A system comprising:
   a control device including control device processing circuitry and control device communication circuitry;
   a targeted device in communication with the control device via messages transmitted by a wireless communication interface, the targeted device including targeted device processing circuitry and targeted device communication circuitry;
   a memory associated with each of the control device and the targeted device for storage of a compressed unique identification assigned to that targeted device, wherein the compressed unique identification has a length less than or equal to that of each of the messages;
   wherein the control device processing circuitry and targeted device processing circuitry each includes circuitry for mixing of the stored compressed unique identification with each message transmitted between the two devices subsequent to receipt of a response signal from the targeted device to an interrogation command from the control device to insure proper communication between the control device and the targeted device.

2. The system in accordance with claim 1, wherein the unique identification is assigned to the targeted device at the time of manufacture and the compressed unique identification is stored in the memory associated with the targeted device at the time of manufacture.

3. The system in accordance with claim 1, wherein the mixing circuitry comprises circuitry for performing a logic function with the compressed unique identification.

4. The system in accordance with claim 3, wherein the logic function performed is XOR.

5. The system in accordance with claim 1, wherein the unique identification is compressed using an error detection scheme.

6. The system in accordance with claim 5, wherein the error detection scheme is a cyclic redundancy check.

7. The system in accordance with claim 5, wherein the compressed unique identification is 2-bytes in length.

8. The system in accordance with claim 1, wherein the processing circuitry associated with each of the control device and the targeted device further comprises circuitry for encoding the mixed result.

9. The system in accordance with claim 8, wherein the mixed result is encoded using a Manchester encoding scheme.

10. A system comprising:
    a control device including control device processing circuitry and control device communication circuitry;
    a targeted device in communication with the control device via messages transmitted by a wireless communication interface, the targeted device including targeted device processing circuitry and targeted device communication circuitry;
    a memory associated with each of the control device and the targeted device for storage of a unique identification assigned to that targeted device;
    wherein the control device processing circuitry and the targeted device processing circuitry each includes additional circuitry to insure proper communication between the control device and the targeted device; for each message transmitted between the two devices subsequent to a response signal transmitted from the targeted device to the control device following an initial interrogation signal from the control device to initiate communication between the two devices, the additional circuitry performing the following functions; (i) when the unique identification of the targeted device has a length that is longer than a length of the message, increasing the length of the message so as to be at least equal to the length of the unique identification; and (ii) mixing the lengthened message with the unique identification.

11. The system in accordance with claim 10, wherein the unique identification is assigned to the targeted device and stored in the memory associated with the targeted device at the time of manufacture.

12. The system in accordance with claim 10, wherein the additional circuitry comprises circuitry for performing a logic function with the lengthened message and the unique identification.

13. The system in accordance with claim 12, wherein the logic function performed is XOR.

14. A method for insuring communication of messages between a control device and a targeted device programmable by the control device via a wireless communication interface, comprising the steps of:
    (a) compressing a unique identification associated with the targeted device to a length less than or equal to a length of each of the messages;
    (b) initiating communication between the two devices by transmitting an interrogation command from the control device to the targeted device;
    (c) in response to receiving the interrogation command at the targeted device, transmitting a response signal thereto that includes the compressed unique identification associated with the targeted device;
    (d) extracting the compressed unique identification from the response signal received by the control device; and
    (e) mixing the compressed unique identification with each subsequent message transmitted between the two devices to insure proper communication between the control device and the targeted device.

15. The method in accordance with claim 14, wherein the unique identification is assigned to the targeted device at the time of manufacture and the compressed unique identification is stored in a memory associated with the targeted device at the time of manufacture.

16. The method in accordance with claim 14, wherein the mixing step (e) comprises, for each of the subsequent messages, performing a logic function with the compressed unique identification.

17. The method in accordance with claim 16, wherein the logic function performed is XOR.

18. The method in accordance with claim 14, wherein in step (a) the unique identification is compressed using an error detection scheme.

19. The method in accordance with claim 18, wherein the error detection scheme is a cyclic redundancy check.

20. The method in accordance with claim 18, wherein the compressed unique identification is 2-bytes in length.

21. The method in accordance with claim 14, further comprising encoding the mixed result.

22. The method in accordance with claim 21, wherein the mixed result is encoded using a Manchester encoding scheme.

23. A method for insuring communication of messages between a control device and a targeted device programmable by the control device via a wireless communication interface, comprising the steps of:
   (a) initiating communication between the two devices by transmitting an interrogation command from the control device to the targeted device;
   (b) in response to receiving the interrogation command at the targeted device, transmitting a response signal thereto that includes a unique identification associated with the targeted device;
   (c) extracting the unique identification from the response signal received by the control device;
   (d) for each subsequent message transmitted between the two devices to insure proper communication between the control device and the targeted device; (i) when the unique identification has a length that is longer than a length of the message, increasing the length of the message so as to be at least equal to the length of the unique identification; and (ii) mixing the lengthened message with the unique identification.

24. The method in accordance with claim 23, wherein the unique identification is assigned to the targeted device and stored in a memory associated with the targeted device at the time of manufacture.

25. The method in accordance with claim 23, wherein the mixing step (d) comprises, for each of the subsequent messages, performing a logic function with the lengthened message and the unique identification.

26. The method in accordance with claim 25, wherein the logic function performed is XOR.

* * * * *